United States Patent [19] [11] 4,020,024
Walraevens et al. [45] Apr. 26, 1977

[54] HALOGENATED POLYETHER-POLYOLS AND POLYURETHANE FOAMS MANUFACTURED FROM THE LATTER

[75] Inventors: René Walraevens, Brussels; André Collin, Ligny, both of Belgium

[73] Assignee: Solvay & Cie, Brussels, Belgium

[22] Filed: Oct. 23, 1974

[21] Appl. No.: 517,396

[30] Foreign Application Priority Data

Oct. 24, 1973 France .............................. 73.38186

[52] U.S. Cl. .................. 260/2.5 AP; 260/77.5 AP
[51] Int. Cl.[2] ......................................... C08J 9/00
[58] Field of Search ............... 260/2.5 AP, 77.5 AP

[56] References Cited

UNITED STATES PATENTS

| | | | |
|---|---|---|---|
| 3,255,126 | 6/1966 | Fuzesi et al. | 260/2.5 AP |
| 3,269,961 | 8/1966 | Bruson et al. | 260/2.5 AP |
| 3,546,145 | 12/1970 | Granger et al. | 260/2.5 AP |

*Primary Examiner*—Lewis T. Jacobs
*Attorney, Agent, or Firm*—Spencer & Kaye

[57] ABSTRACT

Halogenated polyether-polyols lacking terminal primary chlorohydrin and hydroxyl groups are reacted with organic isocyanates to produce semi-rigid or rigid polyurethane foam having excellent physical, mechanical and processing characteristics and good fire-resistance. The polyether-polyols are used individually, as admixtures with each other and/or as admixtures with non-halogenated polyether-polyols.

22 Claims, No Drawings

HALOGENATED POLYETHER-POLYOLS AND POLYURETHANE FOAMS MANUFACTURED FROM THE LATTER

BACKGROUND OF THE INVENTION

Rigid polyurethane foams find many diverse applications in industry and especially in construction and insulation where fire-resistance is desirable and may even be absolutely necessary.

One process for imparting fire-resistance properties to polyurethane foam consists of incorporating into the foam flameproofing additives, such as antimony oxide or halogenated and/or phosphorus-containing compounds, e.g. tris-(dibromopropyl) or tris-(dichloropropyl) phosphates, chlorinated biphenyls and halogenated hydrocarbons. These additives which are not bonded chemically to the base polymer, are incapable of providing uniformly-distributed permanent fire-resistance. Furthermore, as a general rule, they have a plasticizing effect on the foam and, consequently, have an adverse effect on its mechanical properties, and especially on its compressive strength and on its dimensional stability.

Another method for manufacturing fire-resistant polyurethane foam consists of similarly employing halogenated and/or phosphoruscontaining polyols.

French Patent 1,350,425 of Mar. 12, 1963, in the name of Olin Mathieson Corp., describes the use of halogenated polyetherpolyols (manufactured by adding epihalohydrins to monomeric polyhydric alcohols containing at least two hydroxyl groups). Although the cellular polyurethanes resulting from the reaction of organic polyisocyanates with these halogenated polyetherpolyols possess permanent and satisfactory fire-resistance properties, their dimensional stability is only mediocre. Furthermore, these polyether-polyols are unstable when stored in the presence of amine-type compounds usually employed in the formulation of pre-mixes for polyurethane foams.

Belgian Patent 798,674 of Apr. 25, 1973, describes polyether-polyols which are also derived from epichlorohydrin and which have a halogen content which is comparable to that of the halogenated polyetherpolyols disclosed by Olin Mathieson Corp.; these polyether-polyols are characterized by the presence of terminal α-diol groups. The rigid and semi-rigid cellular polyurethanes which are manufactured by employing such halogenated polyether-polyols possess excellent mechanical properties, especially good dimensional stability, in addition to good fire-resistance. The relatively high viscosity of these polyether-polyols nevertheless somewhat complicates their processing.

SUMMARY OF THE INVENTION

The present invention relates to new halogenated polyetherpolyols and to polyurethane foams manufactured therefrom. These halogenated polyether-polyols make it possible to manufacture flameproof polyurethane foams and do not possess the disadvantages of the prior art halogenated polyether-polyols.

The halogenated polyether-polyols according to the invention correspond to the general formula:

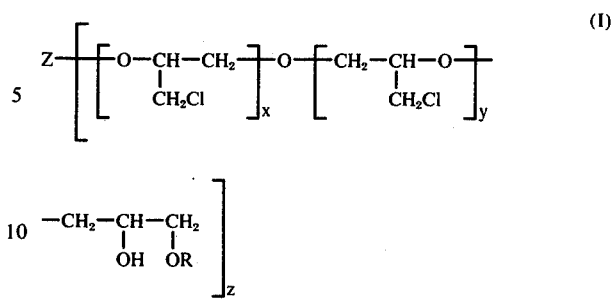

in which $z$ represents a number from 2 to 6, $x$ and $y$ represent numbers from 0 to 7 such that the average value $\overline{x+y}$ per chain is from 0 to 7; $z(\overline{x+y})$, wherein $\overline{x+y}$ represents the average value of $x+y$ throughout the entire molecule, is from 1 to 42; $z$ represents a $C_2$ to $C_6$ aliphatic radical of valency $z$; and R represents a $C_1$ to $C_5$ monovalent aliphatic radical.

The halogenated polyether-polyols according to the invention are characterized by the absence of terminal primary chlorohydrin and hydroxyl groups. They can be stored in the form of pre-mixes containing amine-type compounds. Furthermore, these polyether-polyols possess a viscosity which is comparable to that of unmodified epichlorohydrin oligomers and can be processed easily.

Because of their particular properties, the halogenated polyether-polyols according to the invention find many diverse applications, such as in the manufacture of alkyd resins and adjuvants for epoxy resins. These polyether-polyols are also suitable for manufacturing chlorinated and phosphorus-containing polyether-polyols by reaction with organic and/or inorganic phosphorus compounds, such as phosphorous, phosphoric, pyrophosphoric and polyphosphoric acids, mono- and di-phosphonic acids and their esters.

The halogenated polyether-polyols according to the invention are especially suitable for manufacturing fire-resistant rigid and semi-rigid polyurethane foams. The invention also relates to a process for manufacturing fire-resistant rigid or semi-rigid polyurethane foams.

According to this process, flameproof rigid or semi-rigid polyurethane foams are manufactured by reacting an organic polyisocyanate with at least one polyether-polyol of the general formula I.

An object of this invention is to provide new halogenated polyether-polyols.

A further object is to produce fire-resistant rigid or semi-rigid polyurethane foam from the new halogenated polyether-polyols.

Another object is to provide fire-resistant rigid or semi-rigid polyurethane foam which has good physical properties and good processing properties.

A still further object is to prepare fire-resistant rigid or semi-rigid polyurethanes by reacting an organic isocyanate with a mixture comprising at least one halogenated polyether-polyol and possibly also containing at least one non-halogenated polyether-polyol. Additional objects are readily apparent from the detailed description which follows.

DETAILED DESCRIPTION OF THE INVENTION

Chlorinated polyether-polyols of the invention which are particularly preferred for the manufacture of flameproof rigid polyurethane foams correspond to the above general formula in which $z$, $Z$ and $R$ have the meaning defined above and $x$ and $y$ represent numbers from 0 to 4 such that the average value $\overline{x+y}$ per chain is from 0 to 4 and $z(\overline{x+y})$, wherein $\overline{x+y}$ represents the average value of $x+y$ throughout the entire molecule, is from 1 to 24.

Polyether-polyols which are very particularly preferred for the manufacture of rigid polyurethane foams correspond to the above general formula in which $x$ and $y$ have the meaning defined above, $z$ represents a number from 2 to 4, $Z$ represents an optionally halogenated $C_2$ to $C_4$ aliphatic radical of valency $z$, and $R$ represents an optionally halogenated $C_1$ to $C_3$ monovalent aliphatic radical, the halogen being at least one of chlorine and bromine. Radicals $Z$ and $R$ may be saturated or unsaturated.

The halogenated polyether-polyols according to the invention make it possible to manufacture flameproof polyurethane foams which possess mechanical properties which are similar to, if not better than, those of non-halogenated commercial polyether-polyols.

The halogenated polyether-polyols of the invention are used either individually or in a mixture with one or more other halogenated and/or non-halogenated polyether-polyols in order to manufacture polyurethanes.

The relative proportion of halogenated polyol-polyether in the mixture of polyether-polyols employed can vary to quite a large extent. The self-extinguishing properties of the resulting polyurethane improve as this proportion increases.

It is particularly advantageous to use mixtures comprising halogenated polyether-polyols according to the invention and halogenated polyether-polyols containing terminal $\alpha$-diol groups according to the above-mentioned Belgian Patent 798,674.

By making up such mixtures judiciously, it is possible to adjust the viscosity of the resulting polyether-polyol mixture for the method of processing considered.

Rigid and semi-rigid polyurethane foams according to this invention are manufactured, in a manner which is in itself known, by reacting halogenated polyether-polyol according to the invention (or a mixture of polyether-polyols containing halogenated polyether-polyols according to the invention) with at least one organic polyisocyanate in contact with a foaming agent, one or more catalysts for the reaction and, optionally, water, emulsifiers and/or stabilizers, fillers, pigments and the like.

The halogenated polyether-polyols according to the invention are suitable for manufacturing polyurethane foam by any conventional foaming process, such as the process effected in a single step, referred to as the "one-shot" process, the processes which use a prepolymer or a semi-prepolymer, and the pre-expansion process, referred to as the "frothing" process.

Any organic isocyanate usually employed for manufacturing rigid polyurethane foams is suitable. Isocyanates which are particularly preferred are methylene bis-(4-phenyl-isocyanate) in the pure or partially polymerized state, tolylene diisocyanates in the pure state or in the form of mixtures of isomers, and naphthalene-1,5-diisocyanate.

The theoretical amount of polyisocyanate necessary for manufacturing polyurethane is calculated, in a known manner, as a function of the hydroxyl number of the polyether-polyol or polyether-polyols and, where appropriate, of the water present. A slight excess of polyisocyanate is advantageously employed so as to ensure that the isocyanate number is from about 105 to about 120, since this improves the heat distortion resistance of resulting rigid polyurethane foam.

The catalyst employed can be any one of the catalysts which are known to be useful for this purpose, especially tertiary amines, such as triethylenediamine-(1,4-diazabicyclo-[2,2,2]octane), triethylamine, trimethylamine and dimethylaminoethanol, and metal salts, such as antimony, tin and iron salts. Triethylamine constitutes a catalyst which is particularly preferred.

The amount of catalyst can vary to a certain extent; it affects the mechanical properties of the resulting foam. 0.1 to 3% by weight of catalyst, relative to the polyether-polyol or mixture of polyether polyols, is generally used.

The choice of foaming agent is not critical. All known foaming agents, without exception, are suitable and, especially, water and halogenated hydrocarbons, such as methylene chloride and chloroform, as well as chlorofluoroalkanes, such as trichloromonofluoromethane (R 11), dichlorodifluoromethane (R 12) and trichlorotrifluoroethane (R 13).

The amount of foaming agent can also vary to quite a large extent. 0.1 to 10% by weight of water and/or 1 to 70% by weight of halogenated hydrocarbon, relative to the polyether-polyol or mixture of polyether-polyols, is advantageously used.

Small amounts, preferably from 0.2 to 2% by weight, relative to the polyether-polyol or mixture of polyether-polyols, of a surface-active agent such as ionic and non ionic organic type surfactants and silicones can be used in the reaction mixture to improve the cellular structure of polyurethane foam prepared therefrom.

The method by which the halogenated polyether-polyols, which are the subject of the invention, are prepared is not critical. These halogenated polyether-polyols are, for example, prepared by reacting an epichlorohydrin oligomer corresponding to the general formula:

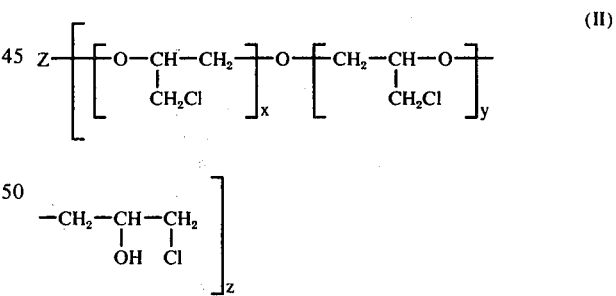

in which $x$, $y$, $z$ and $Z$ have the meanings defined above, with an alkali metal hydroxide, such as sodium hydroxide, at a moderate temperature, in the presence of a $C_1$ to $C_5$ monohydric aliphatic alcohol present in excess, relative to the chlorohydrin groups of the epichlorohydrin oligomer. A variant of this procedure consists of reacting the epichlorohydrin oligomer directly with the corresponding alkali metal alcoholate, still in the presence of excess alcohol, relative to the chlorohydrin groups. These two methods lead to halogenated polyether-polyols according to the invention, together with the formation of an alkali metal chloride as a by-product which is sometimes rather difficult to remove from the reaction mixture. The reaction times are, moreover, rather long.

A preferred method, which is not subject to these disadvantages, consists of the alcoholysis, employing $C_1$ to $C_5$ monohydric aliphatic alcohols, of polyglycidyl ethers of epichlorohydrin oligomers corresponding to the general formula:

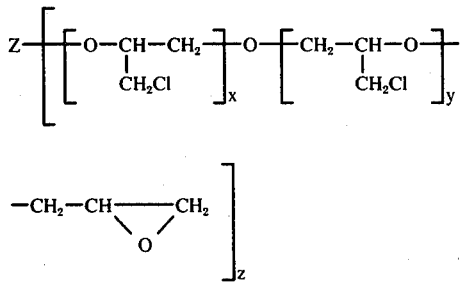

in which $z$ represents a number from 2 to 6; $x$ and $y$ represent numbers from 0 to 7 such that the average value $\overline{x+y}$ per chain is from 0 to 7; $z(\overline{x+Y})$, wherein $\overline{x+y}$ represents the average value of $x+y$ throughout the entire molecule, is from 1 to 42; and Z represents a $C_2$ to $C_6$ aliphatic radical of valency $z$. In this case, it is also advisable to use an excess amount of alcohol, relative to the epoxy groups. 1 to 2 volumes of alcohol per volume of diglycidyl or polyglycidyl ether are advantageously used.

The alcoholysis reaction, moreover, can be accelerated by the use of acid catalysts of the Lewis and Brönsted acid type. In principle, any Lewis or Brönsted acid is suitable, and especially, respectively, boronfluoride and aluminum and antimony chlorides, and nitric, sulfuric and perchloric acids. As far as the protonic acids are concerned, it is advisable to restrict the choice to those particular acids of which the anion is only slightly nucleophilic and, in particular, perchloric acid.

The temperature of the alcoholysis reaction is not critical; it can vary between ambient temperature and the boiling point of the alcohol. In order to reduce the time taken for the reaction, it is desirable to work at the reflux temperature of the alcohol and with vigorous stirring. The progress of the reaction is followed by measuring the residual oxirane oxygen at regular intervals. When the reaction is complete, excess alcohol is removed by evaporation under reduced pressure.

The choice of the $C_1$ to $C_5$ monovalent aliphatic alcohol is not critical. Any $C_1$ to $C_5$ monohydric aliphatic alcohol, without exception, whether it be saturated or unsaturated, halogenated or non-halogenated, is suitable as a reagent for effecting the alcoholysis of polyglycidyl ethers of the epichlorohydrin oligomers. Non-halogenated saturated aliphatic alcohols with a straight or branched chain, such as methanol, ethanol, propan-1-ol, 2-methyl-propan-2-ol (tertiary butyl alcohol) and 3-methyl-butan-1-ol; non-halogenated unsaturated aliphatic alcohols, such as prop-2-en-1-ol (allyl alcohol) and prop-2-yn-1-ol (propargyl alcohol); and halogenated saturated aliphatic alcohols, such as chloroethanol, bromoethanol and chloroisopropanol are, however, preferred. Alcohols which are particularly preferred are methanol, prop-2-en-1-ol, 2-methylpropan-2-ol and chloroethanol.

The procedure described above is suitable for manufacturing "made to measure" halogenated polyether-polyols possessing variable relative proportions of halogen and hydroxyl groups determined by a suitable choice of the original glycidyl ether and monohydric alcohol.

The diglycidyl and polyglycidyl ethers of the epichlorohydrin oligomers are prepared, in a manner which is in itself known, by dehydrochlorination, in an alkaline medium, of chlorinated polyether-polyols possessing terminal chlorohydrin groups, resulting from the oligomerization of epichlorohydrin initiated by water or an optionally halogenated $C_2$ to $C_6$ aliphatic dihydroxylic or polyhydroxylic compound which can be saturated or unsaturated.

A first type of diglycidyl and polyglycidyl ethers, according to the above formula III, comprises those of which the formula contains a non-halogenated radical Z. They are prepared by dehydrochlorination of chlorinated polyether-polyols which result from the catalytic oligomerization of epichlorohydrin initiated by saturated or unsaturated polyols, such as ethylene glycol, propylene glycol and hexamethylene glycol, glycerol, butanetriol and hexanetriol, trimethylolpropane, erythritol and pentaerythritol, mannitol and sorbitol, diethylene glycol and triethylene glycol, dipropylene glycol, but-2-ene-1,4-diol, but-3-ene-1,2-diol, but-2-yne-1,4-diol, but-3-yne-1,2-diol, hexa-1,5-diene-3,4-diol, hexa-2,4-diene-1,6-diol, hexa-1,5-diyne-3,4-diol and hexa-2,4-diyne-1,6-diol.

The polyol initiators which are particularly preferred are but-2-ene-1,4-diol and but-2-yne-1,4-diol, ethylene glycol and glycerol. The use of the latter two initiators leads to the production of diglycidyl and polyglycidyl ethers which correspond to the above general formula III in which Z represents, respectively, the radicals -$CH_2$-$CH_2$- and

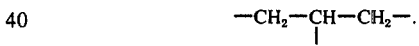

A second type of diglycidyl and polyglycidyl ethers leading to polyether-polyols with a higher halogen content comprises those of which the above formula contains a halogenated radical Z, the halogen being chosen from the group comprising chlorine and bromine. They can be prepared by dehydrochlorination of chlorinated polyether-polyols which result from the catalytic oligomerization of epichlorohydrin initiated by saturated or unsaturated halogenated polyols, such as glycerol monochlorohydrin and glycerol monobromohydrin, 3,4-dibromo-butane-1,2-diol, 2,3-dibromo-butane-1,4-diol, 2,3-dibromo-but-2-ene-1,4-diols, 3,4-dibromo-but-2-ene-1,2-diols, 2,2-bis-bromomethyl-propane-1,3-diol and 1,2,5,6-tetrabromo-hexane-3,4-diol.

The oligomerization of epichlorohydrin can also be initiated by a mixture of brominated and/or unsaturated diols.

The molar ratio of epichlorohydrin to polyol initiator is not critical and can vary within wide proportions. This ratio controls the hydroxyl number of the resulting polyether-polyol.

The oligomerization catalyst can be any one of the acid catalysts known for this type of reaction. Boron tri-fluoride in the free or complexed state is, nevertheless, preferably used.

Diglycidyl and polyglycidyl ethers of brominated epichlorohydrin oligomers can also be prepared by partial or total molecular bromination of the diglycidyl or polyglycidyl ethers of unsaturated epichlorohydrin oligomers prepared by dehydrochlorination in an alkaline medium of the unsaturated chlorinated polyether-polyols resulting from the catalytic oligomerization of epichlorohydrin, initiated by an unsaturated dihydroxylic or polyhydroxylic aliphatic compound.

The halogen content of the polyether-polyols according to the invention which still possess unsaturated bonds can be increased further, and consequently the flame resistance of the polyurethanes which are derived therefrom, by partial or total bromination of these unsaturated bonds. According to this technique, unsaturated polyether-polyols, prepared by alcoholysis of diglycidyl or polyglycidyl ethers of saturated or unsaturated epichlorohydrin oligomers, employing a $C_1$ to $C_5$ unsaturated aliphatic alcohol, are brominated.

The method of bromination of the polyether-polyols and the glycidyl ethers is not critical. It is possible to effect the reaction in a manner which is in itself known, optionally in the presence of a catalyst and an inert solvent, such as chloroform, carbon tetrachloride, methylene chloride and o-dichlorobenzene.

The temperature is generally kept below 50°–60° C.

The amount of bromine employed is not critical. Nevertheless, a practically stoichiometric amount of bromine is preferably used.

The chlorobrominated polyether-polyols which are particularly preferred correspond to the general formula of the polyether-polyols according to the invention in which Z represents the radicals $-CH_2-CHBr-CHBr-CH_2-$ and $CH_2-CBr=CBr-CH_2-$ and R represents the radicals $-CH_3$, $-CH_2-CH=CH_2$,

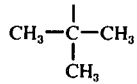

and $-CH_2-CH_2Cl$.

The examples which follow illustrate the invention without limiting it, however. Examples 1 to 3 relate to the manufacture of chlorinated polyether-polyols by alcoholysis, employing methyl alcohol, of, respectively, diglycidyl and triglycidyl ethers of epichlorohydrin oligomers prepared by adding epichlorohydrin to, respectively, ethylene glycol (Examples 1 and 2) and glycerol (Example 3).

Examples 4 and 5 relate to the manufacture of chlorobrominated polyether-polyols by alcoholysis, employing methyl alcohol, of diglycidyl ethers of brominated unsaturated epichlorohydrin oligomers prepared by partial bromination of the products resulting from the addition of epichlorohydrin to but-2-yne-1,4-diol.

Examples 6 to 8 relate to the manufacture of chlorinated polyether-polyols by alcoholysis, employing, respectively, tertiary butyl alcohol, 2-chloro-ethyl alcohol and allyl alcohol, of diglycidyl ethers of saturated epichlorohydrin oligomers prepared by adding epichlorohydrin to ethylene glycol.

The physical properties of the halogenated polyether-polyols manufactured according to Examples 1 to 8 are given in the attached Table 1.

Examples 9 to 12 relate to the manufacture of rigid to semi-rigid flameproof polyurethane foams, by employing halogenated polyether-polyols according to the invention mixed with polyether-polyols according to Belgian Patent 798,674, that is to say, polyether-polyols possessing terminal α-diol groups.

The main physical and mechanical characteristics of the polyurethane foams manufactured according to Examples 9 to 12 are given in the attached Table 2.

The dimensional stability is measured on a 15 × 15 × 1 cm sample of foam, the thickness of which corresponds to the direction of expansion of the foam. This sample is subjected to a temperature of 100° C, at ambient humidity, for 7 days. The 2 medians are then measured in order to calculate the average length of the medians after aging. The dimensional stability is expressed as a variation in the average length of the medians as a percent of the original average length.

EXAMPLE 1

This example relates to the manufacture of a chlorinated, saturated polyether-diol, the molecular weight of which increases to 515.5, characterized in that $Z = -CH_2-CH_2-$, $R = -CH_3$ and $x + y = 1.5$.

500 g, corresponding to 1.10 mols, of the diglycidyl ether derived from epichlorohydrin, manufactured by total dehydrochlorination of the product resulting from the addition of 5 mols of epichlorohydrin to 1 mol of ethylene glycol, together with 350 g of methanol and 1.5 g of perchloric acid in the form of a 70% strength solution are introduced, at ambient temperature, into a 2-liter glass reactor which is immersed in a thermostatically-controlled oil bath and which is equipped with a stirrer and a reflux condenser.

The mixture is heated to the boiling point and is stirred constantly. After 1 hour, measurement of the oxirane oxygen indicates that total conversion of the diglycidyl ether has taken place. The reaction mixture is then cooled and the acidity is neutralized by means of a normal solution of sodium hydroxide. The excess methanol is then removed by evaporation under reduced pressure, and a yellowish liquid which is only very slightly viscous is collected.

EXAMPLE 2

This example relates to the manufacture of a chlorinated saturated polyether-diol, the molecular weight of which increases to 978, characterized in that $Z = -CH_2-CH_2-$, $R = CH_3$ and $\overline{x+y} = 4$.

A procedure similar to that of Example 1 is employed, using 500 g, corresponding to 0.55 mol, of the diglycidyl ether derived from epichlorohydrin, manufactured by total dehydrochlorination of the product resulting from the addition of 10 mols of epichlorohydrin to 1 mol of ethylene glycol.

EXAMPLE 3

This example relates to the manufacture of a chlorinated saturated polyether-triol, the molecular weight of which increases to 541, characterized in that

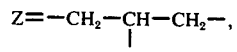

$R = CH_3$ and $\overline{x+y} = 0.66$.

A procedure similar to Example 1 is followed, using 500 g, corresponding to 1.10 mols, of the triglycidyl ether derived from epichlorohydrin, manufactured by total dehydrochlorination of the product resulting from the addition of 5 mols of epichlorohydrin to 1 mol of glycerol.

EXAMPLE 4

This example relates to the manufacture of a chlorobrominated unsaturated polyether-diol, the average molecular weight of which increases to 514.5, characterized in that

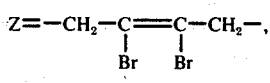

R = —CH$_3$ and $\overline{x+y}$ = 0.5.

The procedure of Example 1 is followed, using 500 g, corresponding to 1.1 mols, of the diglycidyl ether derived from epichlorohydrin, manufactured by total dehydrochlorination of the chlorobrominated polyether-diol prepared by partial bromination of the product resulting from the addition of 3 mols of epichlorohydrin to 1 mol of but-2-yne-1,4-diol.

EXAMPLE 5

This example relates to the manufacture of a chlorobrominated, unsaturated polyether-diol, the molecular weight of which increases to 1,654.5, characterized in that

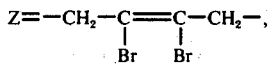

R = CH$_3$ and $\overline{x+y}$ = 6.5.

A procedure similar to that of Example 1 is followed, using 500 g, corresponding to 0.32 mol, of the diglycidyl ether derived from epichlorohydrin, manufactured by total dehydrochlorination of the chlorobrominated polyether-diol prepared by partial bromination of the product resulting from the addition of 15 mols of epichlorohydrin to 1 mol of but-2-yne-1,4-diol.

EXAMPLE 6

This example relates to the manufacture of a chlorinated saturated polyether-diol, the molecular weight of which increases to 599.5, characterized in that Z = —CH$_2$—CH$_2$—,

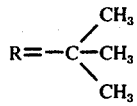

and $\overline{x+y}$ = 1.5.

A procedure similar to Example 1 is followed, using 625 g of tertiary butyl alcohol instead of methyl alcohol.

EXAMPLE 7

This example relates to the manufacture of a chlorinated saturated polyether-diol, the molecular weight of which increases to 612.5, characterized in that Z = —CH$_2$—CH$_2$—, R = —CH$_2$—CH$_2$Cl and $\overline{x+y}$ = 1.5.

A procedure similar to Example 1 is followed, using 500 g of 1-chloro-ethan-2-ol instead of methyl alcohol.

EXAMPLE 8

This example relates to the manufacture of a chlorinated unsaturated polyether-diol, the molecular weight of which increases to 567.5, characterized in that Z = —CH$_2$—CH$_2$—, R = —CH$_2$—CH=CH$_2$ and $\overline{x+y}$ = 1.5.

A procedure similar to Example 1 is followed, using 700 g of allyl alcohol and 1.5 g of boron trifluoride etherate instead of, respectively, methanol and perchloric acid.

EXAMPLE 9

50 g of the saturated chlorinated polyether-diol manufactured according to Example 1, 150 g of the polyether-tetrol corresponding to the general formula:

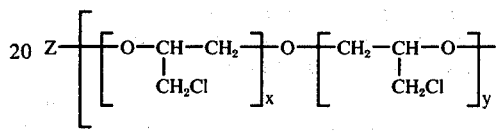

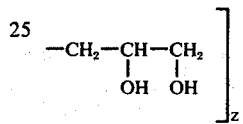

in which Z = —CH$_2$—CH$_2$—, $\overline{x+y}$ = 1.5 and z = 2 and possessing a hydroxyl number of 435 mg KOH/g polyol, 1 g of silicone (copolymer based on siloxane and alkylene oxides) 3 g of triethylamine and 60 g of trichlorofluoromethane (R 11) are introduced successively into a container made of high density polyethylene. The mixture is stirred in order to make it perfectly homogeneous. 194 g of crude methylene bis-(4-phenylisocyanate) are then added. The resulting mixture is stirred for 15 seconds, then poured into a mold and allowed to react at ambient temperature. The cream time and the rising time, counted from the start of stirring the final mixture, increase, respectively, to 16 and 60 seconds.

EXAMPLE 10

A procedure similar to that of Example 9 is followed, but using a 50/50 mixture of the polyether-diol and polyether-tetrol according to Example 9, 2.4 g of triethylamine and 165 g of crude methylene-bis-(4-phenyl-isocyanate). A self-extinguishing rigid foam is formed, the cream tube of which increases to 19 seconds and the rising time of which increases to 90 seconds.

EXAMPLE 11

A procedure similar to that of Example 9 is followed, but using 100 g of the saturated chlorobrominated polyether-diol manufactured in Example 4, 100 g of the polyether-tetrol according to that used in Example 9, 2.4 g of triethylamine and 163 g of crude methylene bis-(4-phenyl-isocyanate).

A self-extinguishing rigid foam is obtained, the cream time of which increases to 18 seconds and the rising time of which increases to 70 seconds.

EXAMPLE 12

A procedure similar to that of Example 9 is followed, but using 100 g of the chlorinated saturated polyether-triol manufactured in Example 3, 100 g of the polyether-hexol corresponding to the general formula given in Example 9 in which $$Z = -CH_2-CH-CH_2-,$$
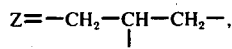

$\overline{x+y} = 2.33$ and $z = 3$ and possessing a hydroxyl number of 295 mg KOH/g polyol, 2.4 g of triethylamine, 54 g of trichlorofluoromethane (R 11) and 152 g of crude methylene bis-(4-phenylisocyanate).

A rigid self-extinguishing foam is formed, the cream time of which increases to 18 seconds and the rising time of which increases to 85 seconds.

It will be understood that the above description of the present invention is susceptible to various modifications, changes and adaptations, and the same are intended to be comprehended within the meaning and range of equivalents of the appended claims.

-continued $$-CH_2-CH-CH_2\underset{OH\ OR}{|\ \ \ \ |}\Bigg]_z$$
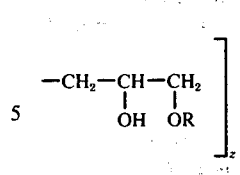

in which $z$ represents a number from 2 to 6; $x$ and $y$ represent numbers from 0 to 7 such that the average value $\overline{x+y}$ per chain is from 0 to 7; $z(\overline{x+y})$, wherein $\overline{x+y}$ represents the average value of $x+y$ throughout the entire molecule, is from 1 to 42; Z represents a $C_2$ to $C_6$ aliphatic radical of valency $z$; and R represents a $C_1$ to $C_5$ monovalent aliphatic radical.

2. A process according to claim 1 wherein Z represents the divalent radical $-CH_2-CH_2-$.

3. A process according to claim 1 wherein Z represents the trivalent radical

Table 1

| Example No. | Viscosity, 25° C, poises | Hydroxyl number, mg KOH/ g polyol | | Elementary analysis, g/kg | | | | | | | | | |
|---|---|---|---|---|---|---|---|---|---|---|---|---|---|
| | | | | Carbon | | Oxygen | | Hydrogen | | Chlorine | | Bromine | |
| | | Calculated | Measured | Calculated | Measured | Calculated | Measured | Calculated | Measured | Calculated | Measured | Calculated | Measured |
| 1 | 11 | 217 | 217 | 442 | 440 | 279 | 273 | 72 | 71 | 207 | 213 | — | — |
| 2 | 63 | 115 | 123 | 417 | 420 | 229 | 225 | 63.5 | 64 | 290.5 | 289 | — | — |
| 3 | 41 | 311 | 303 | 466 | 460 | 325 | 320 | 78 | 75 | 131 | 138 | — | — |
| 4 | 36 | 218 | 207 | 350 | 353 | 218 | 215 | 52 | 50 | 69 | 73 | 311 | 301 |
| 5 | 344 | 69 | 74 | 377 | 375 | 187 | 188 | 54 | 53 | 284 | 286 | 98 | 91 |
| 6 | 82 | 187 | 185 | 500 | 495 | 240 | 235 | 82 | 80 | 178 | 182 | — | — |
| 7 | 61 | 183 | 175 | 411 | 405 | 235 | 238 | 64 | 67 | 290 | 285 | — | — |
| 8 | 8 | 197 | 199 | 486 | 483 | 254 | 250 | 72 | 70 | 188 | 192 | — | — |

Table 2

| Example No. | Apparent specific gravity, kg/m³ | Proportion of closed cells (Scholten method), %* | Compressive strength (ISO Standard Specification R844) kg/cm²** | Dimensional stability after 7 days | |
|---|---|---|---|---|---|
| | | | | 70° C, 95% relative humidity | 100° C ambient humidity |
| 9 | 35.5 | 92 | 2.6 | 6.5 | 6.5 |
| 10 | 37 | 90 | 2.1 | 16.5 | 20 |
| 11 | 34.5 | 92 | 2.2 | 3.5 | 3.0 |
| 12 | 39.4 | 91 | 2.8 | 15.5 | 16.0 |

* Does not contain corrections for the surface cells.
** Forces parallel to the direction of expansion of the foam.

We claim:

1. In the production of a semi-rigid or rigid polyurethane foam from a polyether-polyol, the improvement wherein the polyether-polyol comprises at least one polyether-polyol according to the general formula:

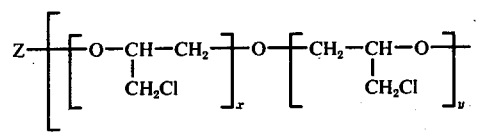

$$-CH_2-CH-CH_2-.$$
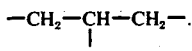

4. A process according to claim 1 wherein Z represents the chlorinated divalent radical $$CH_2Cl-CH-\atop{|\atop CH_2-}$$
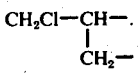

5. A process according to claim 1 wherein Z represents a $C_2$ to $C_6$ saturated or unsaturated brominated aliphatic radical of valency $z$.

6. A process according to claim 5 wherein Z represents the divalent radical $$-CH_2-CH-CH-CH_2-.\atop{|\ \ \ |\atop Br\ \ Br}$$
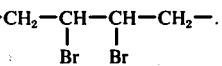

7. A process according to claim 5 wherein Z represents the divalent radical $$-CH_2-C=C-CH_2-.\atop{|\ \ \ |\atop Br\ \ Br}$$
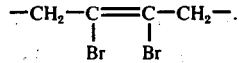

8. A process according to claim 1 wherein Z represents a $C_2$ to $C_6$ unsaturated aliphatic radical of valency $z$.

9. A process according to claim 1 wherein R represents an optionally halogenated $C_1$ to $C_5$ saturated or unsaturated monovalent aliphatic radical.

10. A process according to claim 9 wherein R is a radical selected from the group consisting of —$CH_3$,

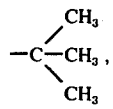

—$CH_2CH_2Cl$ and —$CH_2$-$CH$=$CH_2$.

11. A process according to claim 1 wherein the polyether-polyol is a mixture of non-chlorinated and chlorinated polyether-polyols.

12. An isocyanate/polyether-polyol semi-rigid or rigid polyurethane foam, the polyether-polyol of which comprises a polyether-polyol according to the general formula:

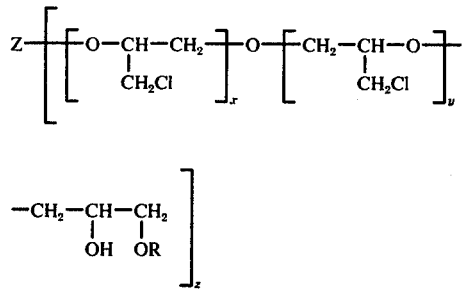

in which z represents a number from 2 to 6; x and y represent numbers from 0 to 7 such that the average value $x + y$ per chain is from 0 to 7; $z(\overline{x+y})$, wherein $\overline{x+y}$ represents the average value of $x + y$ throughout the entire molecule, is from 1 to 42; Z represents a $C_2$ to $C_6$ aliphatic radical of valency z; and R represents a $C_1$ to $C_5$ monovalent aliphatic radical.

13. A foam according to claim 12 wherein Z represents the divalent radical —$CH_2$-$CH_2$—.

14. A foam according to claim 12 wherein Z represents the trivalent radical

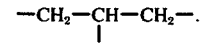

15. A foam according to claim 12 wherein Z represents the chlorinated divalent radical

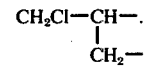

16. A foam according to claim 12 wherein Z represents a $C_2$ to $C_6$ saturated or unsaturated brominated aliphatic radical of valency z.

17. A foam according to claim 16 wherein Z represents the divalent radical

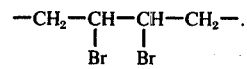

18. A foam according to claim 16 wherein Z represents the divalent radical

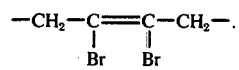

19. A foam according to claim 12 wherein Z represents a $C_2$ to $C_6$ unsaturated aliphatic radical of valency z.

20. A foam according to claim 12 wherein R represents an optionally halogenated $C_1$ to $C_5$ saturated or unsaturated monovalent aliphatic radical.

21. A foam according to claim 20 wherein R is a radical selected from the group consisting of —$CH_3$,

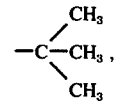

—$CH_2$-$CH_2Cl$ and —$CH_2$-$CH$=$CH_2$.

22. A foam according to claim 12 wherein the polyether-polyol is a mixture of non-chlorinated and chlorinated polyether-polyols.

* * * * *